United States Patent [19]

Cadotte

[11] Patent Number: 4,834,886

[45] Date of Patent: May 30, 1989

[54] PROCESS FOR MAKING ALKALI RESISTANT HYPERFILTRATION MEMBRANE AND RESULTING PRODUCT

[75] Inventor: John E. Cadotte, Minnetonka, Minn.

[73] Assignee: Filmtec Corporation, Minneapolis, Minn.

[21] Appl. No.: 1,488

[22] Filed: Jan. 8, 1987

[51] Int. Cl.$^4$ .................... B01D 13/00; B05D 5/00
[52] U.S. Cl. .................... 210/490; 210/500.36; 210/500.37; 210/500.38; 210/500.42; 427/244; 427/245; 427/253
[58] Field of Search ........... 427/246, 243, 245, 244, 427/353; 210/500.38, 500.41, 500.42, 490, 500.36, 500.37; 521/141

[56] References Cited

U.S. PATENT DOCUMENTS

| | | | |
|---|---|---|---|
| 3,852,388 | 12/1974 | Kimura | 264/41 |
| 3,926,798 | 12/1975 | Cadotte | 427/246 X |
| 4,073,733 | 2/1978 | Yamauchi et al. | 264/49 X |
| 4,279,752 | 7/1981 | Sueoka et al. | 264/49 X |
| 4,366,062 | 12/1982 | Kurihara et al. | 210/651 |
| 4,559,139 | 12/1985 | Uemura et al. | 210/490 |
| 4,609,468 | 9/1986 | Cramm | 210/490 |
| 4,634,531 | 1/1987 | Nakagawa et al. | 210/639 |

FOREIGN PATENT DOCUMENTS 54-118697 9/1979 Japan.
59-080304 5/1984 Japan.

*Primary Examiner*—Evan Lawrence

[57] ABSTRACT

A novel hyperfiltration membrane and process for making the same is described. The membrane is useful for processing copper electroless solutions to concentrate for re-use salts of chelating agents. The membrane can be prepared by crosslinking a water-compatible polymer in the presence of a phosphorus-containing acid, such as phosphoric acid, wherein the acid is present in a sufficient amount to catalyze crosslinking and to form a plurality of pores in the coating when dried.

21 Claims, No Drawings

PROCESS FOR MAKING ALKALI RESISTANT HYPERFILTRATION MEMBRANE AND RESULTING PRODUCT

BACKGROUND OF THE INVENTION

This invention relates to membranes useful to separate solutes or dispersed materials having relatively low molecular weights from higher molecular weight materials.

Porous membranes for separation of minute particles, typically one to ten microns in diameter, from a liquid medium are known. U.S. Pat. No. 4,279,752 describes microporous polyvinyl alcohol membranes prepared by forming membranes containing silica and then extracting the silica. U.S. Pat. No. 4,073,733 discloses porous polyvinyl alcohol membranes prepared by dissolving polyalkylene glycol in polyvinyl alcohol and coagulating the polymer from the solution.

Crosslinked water-soluble polymers are used as an ultrathin solute barrier in a composite membrane disclosed in U.S. Pat. No. 4,559,139. These membranes are useful for separation of potable water via reverse osmosis from brackish water.

U.S. Pat. No. 3,852,388 describes a variety of techniques for making microporous membranes. Phase inversion is a particularly popular technique for making such membranes, but the practical lower limit for the molecular weight discrimination of such membranes is generally 500 or greater.

Japanese Kokai No. 54-118,697 describes a method for making a porous membrane useful to treat body fluids. In this method, a polyvinyl alcohol hollow fiber is coagulated in a caustic solution and then treated with glutaric aldehyde and sulfuric acid to effect crosslinking of the polyvinyl alcohol.

Membranes have been proposed and studied for use in the treatment and reprocessing of industrial by-products. One of the deficiencies of prior art ultrafiltration membranes are that the commercially available polyamide and polyester membranes are not durable in high pH applications. Membranes having improved chemical stability and separation characteristics are actively being sought for use in membrane processes for treating liquids.

SUMMARY OF THE INVENTION

A novel hyperfiltration membrane and process for making the membrane have now been discovered. This hyperfiltration membrane comprises a porous support layer and a discriminating layer affixed to the porous support. The discriminating layer comprises a plurality of pores in a matrix of a water-compatible polymer which has been rendered normally water-insoluble by crosslinking or other means. The resulting membrane exhibits a water flux of at least about 15 gallons per square foot per day (gfd) and a rejection of at least about 60 percent when tested with an aqueous solution of 0.2 percent of a first compound or salt having a molecular weight in the range of about 300 to about 1,000 at 200 psi and 25° C., with the sum of water flux in gfd and rejection of the first compound or salt in percent being equal to at least 90. The membrane also exhibits a NaCl rejection of less than about 30 percent when tested with an aqueous solution of 0.2 percent NaCl at 200 psi and 25° C. Advantageously, the difference between the NaCl rejection and the rejection of the first compound or salt as determined in the aforementioned tests is at least about 50 percent. The recovery for purposes of the aforementioned tests is typically 1 percent.

In another aspect, the invention is a process for making a hyperfiltration membrane. This process comprises first coating at least one major surface of a porous support with a solution comprising water-compatible polymer bearing at least two —OH, —SH, primary amine, secondary amine or amide groups bearing reactive hydrogens. The coating solution further comprises a crosslinking agent selected from the group consisting of aldehydes, ketones and activated vinyl compounds which bear at least two moieties reactive with reactive hydrogens of the polymer and said crosslinking agent is present in an amount effective to render the polymer normally insoluble in water at temperatures in the range from about 20° to about 50° C. The coating solution also includes: (1) an acid which is a solvent or swelling agent for the water-compatible polymer and is normally present in the liquid phase at conditions of coating, and (2) a solvent for the water-compatible polymer. The coating solution is then dried and heat cured so as to crosslink the water-compatible polymer, resulting in a membrane with the aforementioned water flux and rejection of a first compound of a molecular weight greater than about 300 and the aforementioned rejection of NaCl. The acid should be relatively non-volatile, pore-forming when leached out and relatively uniformly dispersed in the coating layer.

In yet another embodiment of this invention, the membranes described herein are used to separate monovalent sodium salts from complex polyvalent sodium salts. This membrane is particularly useful in processing solutions from an electroless copper process to recover EDTA (ethylene diamine tetraacetic acid) salts. Electroless copper plating processes are well known, see, e.g., U.S. Pat. No. 3,475,186. The membrane described herein is much more permeable to formaldehyde and sodium formate than to copper EDTA or sodium EDTA. A solution from a copper-plating process contacting the feed side of the membrane under pressure or some other chemical potential difference will promote selective permeation of sodium formate and formaldehyde through the membrane, leaving a reject stream of concentrated sodium and copper EDTA salts. The concentrated EDTA salts can be readily recycled to the electroless process.

In preferred embodiments of this invention, the resulting membrane exhibits a water flux of at least about 50 gfd and a rejection of at least about 98 percent when tested at 600 psi and 25° C. for copper EDTA (copper salt of ethylene diamine tetraacetic acid) with an aqueous solution prepared from 1 percent $CuSO_4.5H_2O$ and 2 percent $Na_4EDTA$ at a pH 12. The NaCl rejection is preferably less than about 20 percent when tested with an aqueous solution of 0.2 percent NaCl at 200 psi and 25° C. All percentages are by weight unless otherwise indicated.

The term "hyperfiltration" is used herein to denote a pressure-driven membrane process for removal of dissolved inorganic and organic constituents from a liquid solution by selective transport of certain components of the liquid through the membrane. The term "water-compatible polymer" is used herein to refer to polymers soluble to an extent of at least about 0.5 weight percent, more preferably at least about 2 weight percent at 25° C. in water or aqueous solutions containing from about 1 to about 50 weight percent of $C_1$ to $C_4$ alkanols, $C_2$ to $C_4$ alkylene diols or polyols or other water-miscible low molecular weight solvents. "Normally water-insoluble", as used herein, refers to a composition which is substantially insoluble in water at temperatures below 50° C., although some components present may be extractable.

Preferred first compounds or salts used to determine the rejection and flux of the subject membranes are $Na_4EDTA$ for hyperfiltration membranes and dextran or polyethylene glycol for membranes having a higher molecular weight cut-off.

In a preferred embodiment, subject membranes are useful in the separation of solutes having a molecular weight of 100 or less from solutes having a molecular weight of 300 or more. In certain preferred embodiments, the membranes are useful for separation of by-products present in aqueous feeds at a pH of 11 or 12. For example, these membranes can be used to separate iron salts of ethylene diaminetetraacetic acid from sulfate or sulfite salts, as would occur in nitrogen oxide removal from stack gases. The molecular weight cut-off can be raised by use of higher acid concentrations and the resulting membrane used as an ultrafilter or foul-resistant coating for ultrafilters. The membranes are operable as foul-resistant separators for liquid hydrocarbon oils from water. The membrane can also be used to remove impurities from alkaline solutions, e.g., colored impurities or "color bodies" present in caustic solutions.

DETAILED DESCRIPTION OF THE INVENTION

The subject hyperfiltration membranes are composite membranes having a porous support layer with an adherent discriminating layer. Composite membranes are known in the art. See, for example, U.S. Pat. Nos. 4,559,139 and 4,277,344, which are incorporated herein by reference.

The porous support layer can be present in the configuration of a flat sheet, hollow fiber or tubular membrane. The pores in the surface of the support layer to be coated preferably range in size from about 20 to about 1,000 Å, more preferably about 50 to about 500 Å, as determined by scanning electron microscopy. Operable support layers are commercially available and can be made from a variety of polymers including polysulfone, polyvinyl chloride, polycarbonate, polyolefin and polyvinylidene fluoride. Porous supports which tolerate pH in the range from 1 to 13 are preferred. Porous polysulfone supports in a normally wet condition are particularly preferred. Generally, the porous support layer will include a fibrous backing or webbing on which the polymer forming the support was cast.

It is also operable, but not preferred, to use an inorganic support, such as glass, sintered metals or ceramics.

Generally, a major surface of the support layer will be coated with a discriminating layer. In some embodiments of the invention, pretreating the substrate with a surfactant or other agents may be desirable prior to coating. "Major surface", as used herein, refers to a surface of the support representing a significant portion of the support's total surface area and which can be secured so that the major surface separates a first space from a second space. For example, a flat sheet support can be coated on one side with a discriminating layer and then used in a spiral or plate and frame membrane device. A hollow fiber can be coated down either the lumen of the fiber or on the external surface of the fiber. Optionally, more than one major surface of a support can be coated with a discriminating layer, but this is not generally desirable. Typically, the discriminating layer will be in direct contact with the fluid feed.

The support layer is coated with a solution containing a water-compatible polymer, a crosslinking agent and an acid, where said acid both catalyzes crosslinking and contributes to pore formation in the crosslinked polymer. Any convenient technique known in the prior art can be used to apply the coating. For example, the support can be dipped in, sprayed with or wiped with the coating solution. After coating the surface, excess liquid is conveniently removed with a roller or via conventional techniques. Desirably, the coating should be as thin as possible, while still maintaining its integrity. In general, the flux through the discriminating layer is inversely proportional to its thickness. Preferably, the discriminating layer, after drying, is in the range from about 500 to about 5,000 Å thick, more preferably about 1,000 to about 2,000 Å.

The solvent used for the coating solution is preferably water. Lower ($C_1$ to $C_3$) alkanols, polyethers, polyols or other similar organic solvents are also operable as solvents or co-solvents, provided that the water-compatible polymer, crosslinker and acid are soluble in the solvent to the desired concentration and the solvent does not deleteriously affect the reaction of the polymer with the crosslinker. Co-solvents, surfactants or other additives may be desirable in minor amounts to decrease foaming, enhance film-forming or improve other properties of the coating solution.

Water-compatible polymers are preferably those exhibiting good chemical stability and desired membrane characteristics. Illustrative polymers include acrylamide polymers, cellulosic polymers bearing a plurality of hydroxyl groups, polyethyleneimine and other polymers or copolymers which bear reactive hydrogen moieties and which are water-compatible. Particularly preferred polymers are vinyl polymers bearing a plurality of hydroxyl groups, such as partially or substantially completely hydrolyzed polyvinyl acetate and vinyl acetate copolymers. Monomers which can operably be used in the vinyl acetate copolymers include crotonic acid and acrylic acid. Polyvinyl alcohol or a vinyl acetate polymer or copolymer which has been hydrolyzed to the extent necessary to render the polymer water-compatible are especially preferred. More preferably, the polymer is a polyvinyl alcohol which is about 75 to about 96 percent hydrolyzed, most preferably about 88 percent hydrolyzed.

Preferred water-compatible polymers can be dissolved in an aqueous solution in a concentration of at least 1 weight percent. To this polymer solution can be added 1 weight percent phosphoric acid without coagulation or precipitation. This acid-containing polymer solution, when dried, will appear as a single phase film with no separate acid phase visible to the unaided eye.

The molecular weight of the polymer is generally not critical, so long as the polymer is water-compatible and will readily coat as a film on the support layer. Optimum molecular weights may vary depending on the polymer, the substrate and solvent. If a polymer of a particular molecular weight is preferred in an embodiment of this invention, this can readily be determined empirically. Generally, polyvinyl alcohols having a molecular weight in the range from about 10,000 to about 125,000, as determined by gel permeation chromatography, are preferred in aqueous coating solutions.

The molecular weights used herein are number average molecular weights.

The water-compatible polymers used in the coating solutions must be rendered normally water-insoluble after coating. Preferably, the water-compatible polymer in the coating is reacted with a crosslinking agent to render it water-insoluble.

The crosslinking agents used herein are compounds bearing at least two substituents reactive under acid pH conditions with the active hydrogen groups of the water-compatible polymer. Compounds bearing a plurality of aldehyde groups, such as glyoxal, glutaraldehyde, formaldehyde derivatives and the like, or bearing a plurality of ketone groups, such as 1,4-cyclohexanedione, are operable. Preferred crosslinking agents are glyoxal and glutaraldehyde. The crosslinking agent should produce a degree of crosslinking effective to render the water-compatible polymer normally water-insoluble.

The acid present in the coating solution should be essentially non-volatile and should not crystallize at the conditions of coating and drying. The acid should be sufficiently compatible with the water-compatible polymer to swell or dissolve the polymer. Operable acids include phosphorus-containing protic acids of various oxidation states, with phosphoric acid being preferred. Of course, compounds which will form phosphoric acid in aqueous solutions are also operable, such as polyphosphoric acid. Illustrative acids include hypo-, meta-, ortho- and pyro-phosphorous acid and hypo-, meta-, ortho- and pyro-phosphoric acid.

The acid is believed to serve as a pore-forming agent. It appears likely that some polyphosphoric acid is formed during curing, but the invention herein is not so limited. Optionally, other leachable pore-forming agents can be used in addition to the acid, but generally are not desirable.

The acid pore-forming agent will itself catalyze the crosslinking reaction. When low temperature crosslinking is desired, additional catalysts can be used. Carboxylic acids incorporated in the polymer coating may also catalyze the crosslinking reaction, but in general do not possess significant catalytic activity. Sulfuric acid, trifluoromethylsulfonic acid, copper salts and zinc salts are operable as co-catalysts. The co-catalysts can undesirably increase the rejection by the membrane of monovalent salts or sulfate salts.

The relative concentrations of the components present in the coating solution can be varied over a fairly wide range. The maximum and minimum concentrations conveniently used will vary dependent upon the solvent, polymer, cure temperature and other parameters used and components present. Because of the viscosity of the solution and thickness of the cured coating at high concentrations of polymer, the polymer is preferably present at a level of less than about 10 parts by weight, more preferably less than about 5 parts by weight and most preferably less than about 2 parts by weight. For convenience in removal of solvent during drying of the coating solution and to form films with good integrity, it is preferable that the solution contain at least about 0.1 part by weight, more preferably at least about 0.5 part by weight and most preferably at least about 1 part by weight polymer.

The weight ratio of acid pore-forming agent to polymer in the coating solution is preferably in the range from about 1:2 to about 20:1, more preferably about 1:1 to about 10:1 and most preferably about 3:2 to about 5:1.

In general, pore size will increase with increasing concentrations of acid. Preferably, from about 0.5 to about 10 parts by weight, more preferably from about 2 to about 6 parts by weight, acid pore-forming agent is present in the coating solution. Even greater concentrations of acid can be used if a higher molecular weight cut-off is desired. For example, a weight ratio of about 8:1 of phosphoric acid to polyvinyl alcohol can be conveniently used to make an ultrafiltration membrane. Too high a concentration of phosphoric acid can be deleterious to formation of a dried sheet and membrane properties. The maximum operable acid concentration can be determined empirically.

The ratio of reactive sites on the polymer to reactive groups on the crosslinking agent is preferably in the range from about 100:1 to about 1:10, more preferably about 20:1 to about 1:5, in the coating solution. The degree of crosslinking generally is not believed critical, so long as the polymer is rendered water-insoluble. Pore size of the membrane product generally decreases with increasing amounts of crosslinking agent, at least until an excess of the crosslinker is employed.

In one preferred embodiment of the invention, glyoxal is employed in the coating solution as a crosslinking agent in a concentration of from about 0.04 to about 4 parts by weight, more preferably about 0.1 to about 2 parts by weight. In another preferred embodiment of the invention, glutaraldehyde is employed as a crosslinking agent in a concentration in the range from about 0.025 to about 1 part by weight, more preferably about 0.05 to about 0.5 part by weight. It should be noted that these aldehydes are volatile and some aldehyde may evaporate during the curing process.

If a low temperature cure is desired, a co-catalyst for the crosslinking reaction can be added to the coating solution. Operable co-catalysts include copper salts, zinc salts and other catalysts for the crosslinking reaction known in the art. Sulfuric acid is the preferred co-catalyst, when phosphoric acid is the principal pore-forming agent. From about 0.01 to about 2.0, preferably about 0.1 to about 1, parts by weight co-catalyst are generally desirable if a co-catalyst is used.

In a preferred embodiment of the invention, polyvinyl alcohol is used as the polymer with a glyoxal or glutaraldehyde crosslinking agent. Acetal groups are believed to be the predominant crosslink. In general, some hydroxyl groups will be present in the crosslinked polymer.

The coated support layer is dried at temperatures sufficient to promote crosslinking of the coating solution. Reduced pressures are operable during drying, but atmospheric pressure is generally convenient. Depending upon the reactants, catalyst, concentration of reactants and heat resistance of the microporous support, temperatures in the range of from about 60° to about 150° C. may be operable, with temperatures in the range from about 90° to about 120° C. being generally preferred.

Porous substrate sheets commonly contain a nonwoven backing on which they are cast. Some backing materials, such as polypropylene, may be adversely affected at high cure temperatures. Use of a co-catalyst may permit lower cure temperatures, but care must be taken not to undesirably increase rejection by the membrane of low molecular weight materials.

The cure time generally will decrease as the cure temperature increases. Cure times in the range of from about 1 to about 30 minutes have been use with preferred coating solutions. The optimum time and temperature for curing a specific coating solution can be readily determined empirically.

The coating, after drying, is preferably washed or immersed in water to leach out the acid present in the coating. Alternatively, the acid can be leached out during the initial operation of the membrane.

The membranes of this invention can be fabricated by conventional techniques into membrane devices of configurations known in the art. Flat sheet membranes can be utilized in plate-and-frame or spiral devices. Hollow fiber membranes and tubular membranes can be assembled in parallel or bias-wrap configurations known in the art. See, for example, U.S. Pat. Nos. 4,080,296; 3,422,008 and 3,228,877. Spiral devices containing channel spacers and other components which will tolerate a pH of 12, are especially preferred.

The subject membranes can be used as supports for additional discriminating layers, if desired. Protective coatings or rejection enhancing coatings are also operable, but not preferred.

The membranes described herein can generally be operated over a wide range of feed solution compositions, pH ranges, transmembrane pressures and feed temperatures. A higher pressure of the feed side than the permeate side of the membrane is conveniently used as a driving force for transport through the membrane. The upper limit on transmembrane pressure is generally determined by the physical properties of the membrane. The lower limit on pressure is determined by the chemical potential difference required across the membrane. Transmembrane pressures in the range from about 50 to about 1,000, preferably about 100 to about 600, pounds per square inch gauge (psig) are generally preferred.

The operating temperature should be sufficiently high to maintain the feed and permeate in a fluid state. The upper limit on temperature is determined by the heat sensitivity of the components of the membrane device. Temperatures in the range from about 0° to about 50° C. are generally convenient.

The pH of the feed solution can be any pH which the membrane and associated components will tolerate. The composition of the discriminating layer is advantageously selected, so as to tolerate the pH and composition of the feed solution. The preferred crosslinked polyvinyl alcohol coatings can tolerate a pH in the range from about 6 to about 13.

The membranes described herein are in general sufficiently porous that most of the water flux through the membrane occurs via flow through the pores. The pores are advantageously of a size such that chloride or sulfate salts of alkali metals pass through the membrane readily relative to higher molecular weight solutes or colloidal suspended materials which are rejected. Advantageously, the membranes are normally substantially nonionic, i.e., the discriminating layer does not bear ionic groups at a pH of 7. Membranes can be made which are tolerant of pH 12 feed. These membranes also have utility in removal of oil emulsions from water, waste treatment processes and in processing of food.

The following examples are presented to illustrate but not otherwise limit the invention.

Preparation of Support Layer

A polyester non-woven fabric (from Filtration Sciences Corporation, sold as HOLLYTEX® 3329) was coated with a solution of 90 parts dimethyl formamide and 10 parts dimethyl sulfoxide containing 19.5 percent by weight of a polysulfone (Union Carbide UDEL® P3500 polysulfone) with a coating knife. The coated fabric was immediately quenched in water at 15° C. The film was cut into 6 inch by 12 inch pieces, secured to glass with adhesive tape and pressed with a hand roller to remove surface water.

Where the membrane is to be subject to high pH environments, a polypropylene non-woven fabric, such as VILEDON® FO 2430, available from Carl Freudenberg (Viledon Nonwovens Division), is preferred for the support layer. The polypropylene web can be coated in generally the same manner as the polyester.

EXAMPLES 1-4, COMPARATIVE EXPERIMENTS A-B

Dilute aqueous solutions of polyvinyl alcohol (PVOH), phosphoric acid ($H_3PO_4$) and optionally glyoxal or sulfuric acid ($H_2SO_4$) were prepared as tabulated in Table I. The composition is indicated in weight percent. The polyvinyl alcohol was obtained from Air Products and Chemicals Inc. and was 99.3 percent hydrolyzed with a viscosity of 55 to 65 centipoise for a 4 weight percent solution at 25° C.

The solution was spread on the support layer affixed to glass. Excess solution was removed by pressing the coated support with a rubber hand roller. The glass plate with the coated support was placed in a 100° C. forced air oven for the tabulated time.

The dried membrane was removed from the glass and placed in a plate and frame test apparatus of conventional design. The rejection and flux of the membrane was determined at 200 psi and 25° C. for an aqueous solution containing 0.2 weight percent NaCl and one containing 0.2 percent $Na_4EDTA$. The parameters and results are tabulated in Table I.

TABLE I

| Example | Comp.* Experiment | Coating Composition (Weight Percent) | | | | Cure (Minutes) | 0.2% NaCl | | 0.2% $Na_4EDTA$ | |
|---|---|---|---|---|---|---|---|---|---|---|
| | | $H_3PO_4$ | PVOH | $H_2SO_4$ | Glyoxal | | Flux (gfd) | Rej. (%) | Flux (gfd) | Rej. (%) |
| — | A | 5 | 1 | — | — | 15 | 99 | 8 | 85 | 57 |
| — | B | 5 | 1 | 1 | — | 15 | 63 | 38 | 56 | 80 |
| 1 | — | 3.93 | 0.926 | — | 1.11 | 1 | 76 | 2 | 78 | 43 |
| 2 | — | 3.93 | 0.926 | — | 1.11 | 5 | 46 | 8 | 42 | 53 |
| 3 | — | 3.93 | 0.926 | — | 1.11 | 10 | 51 | 12 | 48 | 65 |
| 4 | — | 3.93 | 0.926 | — | 1.11 | 15 | 29 | 17 | 25 | 80 |

*Not an embodiment of this invention.

In Comparative Experiment A, the rejection of the $Na_4EDTA$ was not as great as desired. The presence of $H_2SO_4$ in the coating of Experiment B undesirably increased the NaCl rejection. Examples 1-4 disclose membranes which exhibit excellent water flux and good rejection of polyvalent sodium salts without greatly increasing the rejection of monovalent sodium salts.

The use of a crosslinker in Examples 1 and 2 provided a relatively low Na$_4$EDTA rejection because of the short cure times relative to Examples 3 and 4.

The membranes in Examples 1 and 2 would be more useful for separation of a higher molecular weight material than Na$_4$EDTA from a low molecular weight salt, such as NaCl. The resulting membranes generally have a higher rejection for copper EDTA salts than Na$_4$EDTA.

EXAMPLE 5

In a manner generally similar to Example 4, an aqueous coating of 3.93 weight percent H$_3$PO$_4$, 0.926 weight percent PVOH and 1.11 weight percent glyoxal was applied to a porous polysulfone support and dried at 90° C. for 15 minutes. The polysulfone support in this instance was cast on a polypropylene non-woven web.

The resulting membrane was tested in a plate and frame apparatus. The water flux of the membrane was determined to be 81 gfd and NaCl rejection was 12 percent, when the membrane was tested with a 0.2 weight percent aqueous solution of NaCl at 200 psi and 25° C. The water flux was 60 gfd and Na$_4$EDTA rejection was 89 percent, when the membrane was tested with a 0.2 weight percent aqueous solution of Na$_4$EDTA at 200 psi and 25° C.

EXAMPLE 6

In a manner generally similar to Example 5, except that 1 weight percent sulfuric acid was present in the coating solution, a polysulfone substrate was coated and dried. When the resulting membrane was tested with a 0.2 percent solution of NaCl at 100 psi, a water flux of 14.8 gfd and a NaCl rejection of 21 was determined. The water flux and Na$_4$EDTA rejection with a 0.2 percent solution of Na$_4$EDTA at 100 psi were 18.0 gfd and 95.3 percent, respectively.

In a comparison with Example 5, it can be seen that the sulfuric acid catalyst resulted in a decreased water flux and increased salt rejection.

EXAMPLES 7-12

In a manner generally similar to Example 5, six porous polysulfone substrates were coated with an aqueous solution of 3.93 weight percent H$_3$PO$_4$, 0.926 weight percent PVOH and 1.11 weight percent glyoxal. In additional experiments, 1 weight percent sulfuric acid was also present in the coating solution. The coated substrates were then cured for about 15 minutes in a forced air oven at a temperature in the range from about 90° to about 120° C.

The flux and rejection of the resulting membranes were tested with aqueous solutions of either 0.2 percent NaCl or 0.2 percent Na$_4$EDTA at 100 psi. The cure temperature and membrane characteristics for each membrane are presented in Table II.

TABLE II

| | | 0.2% NaCl | | 0.2% Na$_4$EDTA | |
|---|---|---|---|---|---|
| Example | Cure Temp. (°C.) | Flux (gfd) | Rej. (%) | Flux (gfd) | Rej. (%) |
| 7 | 90 | 52 | 7 | 51 | 85 |
| 8 | 120 | 15 | 28 | 19 | 94 |
| 9 | 90 | 12 | 39 | 16 | 95 |
| 10 | 100 | 6 | 60 | 9 | 97 |
| 11 | 110 | 8 | 64 | 12 | 97 |
| 12 | 120 | 3 | 65 | 5 | 96 |

The higher drying temperature in Example 8 decreased the flux and increased the rejection of the membrane relative to that obtained in Example 7. The presence of sulfuric acid in Examples 9-12 significantly increased the NaCl rejection even at a 90° C. cure temperature. The resulting membrane in Examples 9-12 is useful as a "loose" reverse osmosis membrane, i.e., a membrane with only a moderate sodium chloride rejection. Shorter cure times would have to be used with the sulfuric acid catalyst to obtain the desired membrane properties.

EXAMPLES 13-20

In a manner generally similar to Example 1, dilute aqueous solutions of 1 weight percent polymer, 3.9 percent phosphoric acid, 3.9 percent phosphorous acid or 7.8 percent phosphoric acid, 1.2 percent glyoxal crosslinker (except Example 12 which substituted 0.5 percent glutaraldehyde) were coated on a porous polysulfone support. The coated support was then heat cured at 100° C. for 15 minutes. The polymers used were: (a) PVOH, (b) hydrolyzed 90/10 vinylacetate/methacrylic acid copolymer, (c) poly(2-hydroxyethyl methacrylate), (d) hydrolyzed 90/10 vinylacetate/crotonic acid copolymer and (e) a hydrolyzed vinylacetate/acrylic ester copolymer in which the unhydrolyzed copolymer is more than 50 percent vinylacetate (sold by Monsanto Company as Gelva® TS100).

The water flux in gfd and percent salt rejection were determined for (A) 0.2 percent NaCl at 200 psi, (B) 0.2 percent Na$_4$EDTA at 200 psi and (C) a mixture of 1 weight percent Na$_4$EDTA and CuSO$_4$.5H$_2$O at 600 psi. The reverse osmosis test results and other parameters for each membrane are presented in Table III.

TABLE III

| | | | RO Test Data | | | | |
|---|---|---|---|---|---|---|---|
| | | | A | | B | | C |
| Ex. | Polymer | Acid | Flux | Rej. | Flux | Rej. | Flux | Rej. |
| 13 | a | 3.9% H$_3$PO$_4$ | 40 | 22 | 41 | 94 | 102 | 99 |
| 14 | a | 3.9% H$_3$PO$_4$* | 91 | 22 | 93 | 94 | 179 | 98 |
| 15 | a | 3.9% H$_3$PO$_3$ | 44 | 26 | 41 | 92 | 134 | 98.6 |
| 16 | a | 3.9% H$_3$PO$_4$ | 93 | 23 | 136 | 92 | 240 | 93 |
| 17 | e | 3.9% H$_3$PO$_4$ | 164 | 9 | 113 | 86 | 180 | 81 |
| 18 | b | 3.9% H$_3$PO$_4$ | 82 | 19 | 69 | 93 | 134 | 96.7 |
| 19 | c | 7.8% H$_3$PO$_4$ | 26 | 15 | 22 | 88 | 51 | 84 |
| 20 | d | 7.8% H$_3$PO$_4$ | 83 | 16 | 76 | 90 | 152 | 97 |

*1 percent trifluoromethane sulfonic acid added.

The data presented in Table III confirms the low sodium chloride rejection and high rejection for Na$_4$EDTA displayed by the subject membranes.

What is claimed is:

1. A process for making a hyperfiltration membrane comprising the steps of:
   (a) coating at least one major surface of a porous support with a solution comprising:
       (i) a water-compatible polymer bearing a plurality of —OH, —SH, primary or secondary amine or amide groups bearing reactive hydrogens;
       (ii) a crosslinking agent selected from the group consisting of di- or polyfunctional aldehydes, ketones and activated vinyl compounds in an amount effective to render the polymer insoluble in water;
       (iii) a phosphorus-containing acid which is a solvent or swelling agent for the water-compatible polymer and is present in the liquid phase at the conditions of coating in an amount effective to catalyze crosslinking and to form a plurality of pores in the coating when dried; and (iv) a solvent for the water-compatible polymer; and (b) drying the coating so as to crosslink the water-compatible polymer with the crosslinking agent and form in the coating a plurality of pores.

2. The process as described in claim 1 wherein the solvent for the water-compatible polymer is water.

3. The process as described in claim 1 wherein the water-compatible polymer is a polymer or copolymer of vinyl acetate wherein at least about 65 percent of the acetate groups have been hydrolyzed.

4. The process as described in claim 2 wherein the water-compatible polymer is polyvinyl alcohol.

5. The process as described in claim 3 wherein the acid is phosphorous acid, phosphoric acid or polyphosphoric acid.

6. The process as described in claim 3 wherein the acid is phosphoric acid.

7. The process as described in claim 1 wherein the crosslinking agent is a compound bearing at least two aldehyde groups.

8. The process as described in claim 6 wherein the crosslinking agent is glyoxal or glutaraldehyde.

9. The process as described in claim 8 wherein the porous support is porous polysulfone.

10. The process as described in claim 1 wherein the resulting membrane has a water flux of at least about 15 gfd and a rejection of at least about 60 percent when tested with an aqueous solution of 0.2 percent $Na_4EDTA$ at 200 psi and 25° C., and a NaCl rejection of less than about 30 percent when tested with an aqueous solution of 0.2 percent NaCl at 200 psi and 25° C.

11. The process as described in claim 9 wherein the resulting membrane has a NaCl rejection of less than about 20 percent when tested with an aqueous solution of 0.2 percent NaCl at 200 psi and 25° C.

12. The process as described in claim 11 wherein the resulting membrane exhibits a water flux of at least about 50 gfd and a rejection of at least about 98 percent for copper salts of EDTA when tested at 600 psi and 25° C. at a pH of 12 with an aqueous solution prepared with 2 percent $Na_4EDTA$ and 1 percent $CuSO_4.5H_2O$.

13. The process as described in claim 3 wherein the weight ratio of acid to polymer in the coating solution is in the range from about 1:2 to about 20:1.

14. The process as described in claim 13 wherein the acid concentration of the coating solution is in the range from about 0.5 to about 10 parts by weight.

15. The process as described in claim 14 wherein the ratio of reactive sites on the polymer to reactive sites on the crosslinking agent is in the range from about 20:1 to about 1:5.

16. The process as described in claim 15 wherein the coating solution further comprises an effective amount of a co-catalyst for the crosslinking reaction.

17. The process as described in claim 16 wherein the co-catalyst is sulfuric acid.

18. The process as described in claim 1 wherein the process further comprises the step of contacting the membrane with water to leach out the acid present in the coating.

19. The membrane made by the process of claim 3.

20. The membrane made by the process of claim 8.

21. The membrane made by the process of claim 11.

* * * * *